United States Patent [19]

Tang et al.

[11] Patent Number: 5,510,492
[45] Date of Patent: Apr. 23, 1996

[54] PROCESS OF PREPARING PYRAZOLO [1,5-B][1,2,4] TRIAZOLES

[75] Inventors: Ping-Wah Tang; Terrence C. Mungal, both of Rochester, N.Y.

[73] Assignee: Eastman Kodak Company, Rochester, N.Y.

[21] Appl. No.: 142,112

[22] Filed: Oct. 28, 1993

Related U.S. Application Data

[63] Continuation of Ser. No. 841,462, Feb. 26, 1992, abandoned.

[51] Int. Cl.$^6$ ................................................ C07D 487/04
[52] U.S. Cl. .................................... 548/262.4; 548/371.7
[58] Field of Search ............................ 548/371.7, 262.4

[56] References Cited

U.S. PATENT DOCUMENTS

| | | |
|---|---|---|
| 4,540,654 | 9/1985 | Sato et al. . |
| 4,621,046 | 11/1986 | Sato et al. . |
| 4,705,863 | 11/1987 | Sato et al. . |
| 4,921,968 | 5/1990 | Yokoyama et al. .................. 548/262.4 |
| 5,262,542 | 11/1993 | Tang et al. ............................ 548/262.4 |

FOREIGN PATENT DOCUMENTS

| | | |
|---|---|---|
| 287265 | 10/1988 | European Pat. Off. . |
| 294785 | 12/1988 | European Pat. Off. . |
| 172982 | 9/1985 | Japan . |
| 60-215687 | 10/1985 | Japan . |
| 63-218665 | 9/1988 | Japan . |
| 1-025765 | 1/1989 | Japan . |

*Primary Examiner*—Robert W. Ramsuer
*Attorney, Agent, or Firm*—Arthur E. Kluegel

[57] ABSTRACT

A process of preparing an N-(4-chloropyrazolyl) amidoxime comprises reacting a compound of the formula

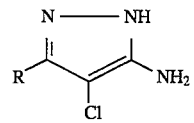

with a compound of the formula

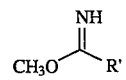

to obtain compounds of formulae (IIIA) and/or (IIIB)

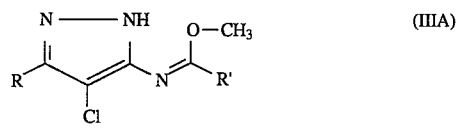

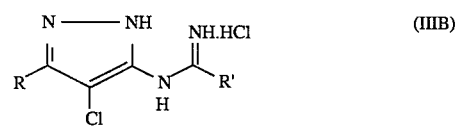

and converting the compounds of formulae (IIIA) and/or (IIIB) to an amidoxime of formula (II)

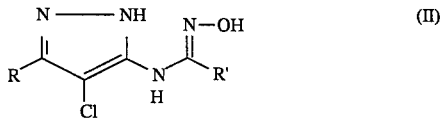

wherein R and R' independently represent hydrogen or a substituent.

4 Claims, No Drawings

PROCESS OF PREPARING PYRAZOLO [1,5-B] [1,2,4] TRIAZOLES

This application is a continuation of U.S. application Ser. No. 07/841,462 filed Feb. 26, 1992, now abandoned.

BACKGROUND OF THE INVENTION

The present invention relates to a process of preparing N-(4-chloropyrazolyl) amidoximes which are useful as intermediates in the preparation of 1H-pyrazolo[1,5-b] [1,2,4] triazole compounds of formula (I):

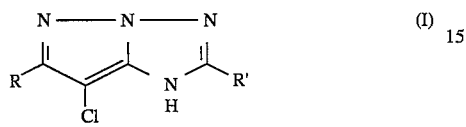

Formula (I) includes pyrazolotriazole compounds which are 1H-pyrazolo[1,5-b][1,2,4] triazole dye-forming couplers employed in photographic silver halide materials, wherein R and R' are independently hydrogen or a coupler substituent known in the photographic art which does not adversely affect the desired properties of the coupler. Such couplers are described in European Patent 177,765 and U.S. Pat. No. 4,540,654, for example. Additionally, formula (I) includes compounds wherein R or R' is a reactive group which can be converted to the coupler substituent, thereby providing a dye-forming 1H-pyrazolo [1,5-b][1,2,4] triazole coupler.

The N-(4-chloropyrazolyl) amidoximes are represented by formula (II)

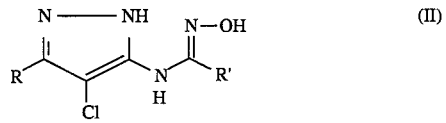

wherein R and R' are independently hydrogen or a substituent as defined for formula (I).

The pyrazolotriazoles of formula (I) can be obtained from the amidoximes of formula (II) by the following cyclization reaction.

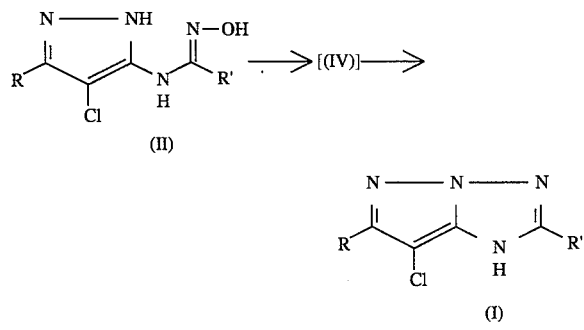

When amidoxime compounds which do not contain the 4-substitution on the pyrazole ring are subjected to cyclization to form the formula (I) compounds, undesirable by-products are formed. This complicates the purification of the desired formula (II) compounds and significantly lowers the yield.

Japanese kokai 63-218,665 discloses a method of making N-(4-chloropyrazolyl)amidoximes. This method involves an initial step wherein an amidoxime which contains no substitution at the 4-position of the pyrazole ring is formed, and in a subsequent step, the 4-chloro substituent is introduced to the amidoxime. However, this process has an unsatisfactory yield.

Accordingly, an object of the present invention is to provide an improved method for the production of amidoximes of formula (II). The process involves relatively simple reaction conditions and isolation procedures, and the amidoximes are produced at high yield.

SUMMARY OF THE INVENTION

The process according to the present invention comprises reacting a compound of the formula (V)

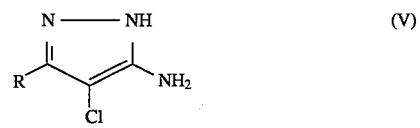

with a compound of the formula (VI)

to obtain compounds of formulae (IIIA) and/or (IIIB)

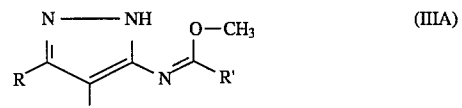

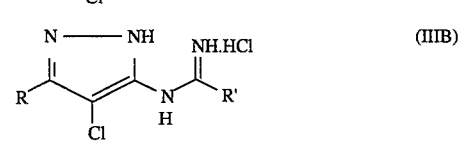

and converting the obtained compounds to the compound of formula (II).

R and R' in the above formulae independently represent hydrogen or a coupler substituent known in the photographic art. Additionally, R or R' may represent a reactive group which can be converted to the coupler substituent.

DESCRIPTION OF THE PREFERRED EMBODIMENTS

In a preferred embodiment, the process is represented by the following scheme:

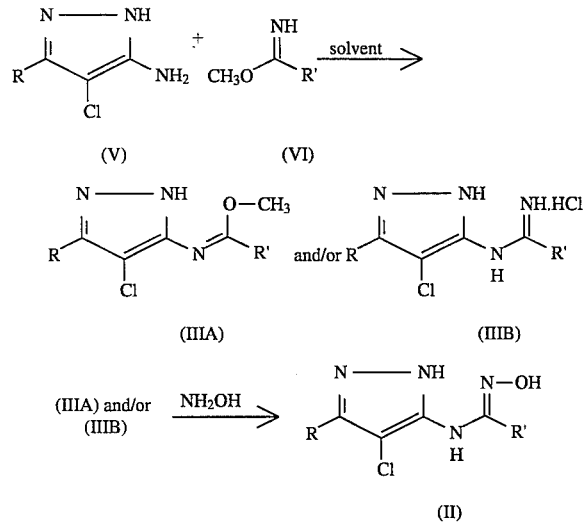

Accordingly, the process is a relatively simple one-pot, 2-step process, wherein compounds of formulae (IIIA) and/or (IIIB) are formed from available reactants, and the compounds of formulae (IIIA) and/or (IIIB) are converted to the desired amidoxime.

The preparation of the amidoxime of formula (II) from the aminopyrazole of formula (V) and the imidate of formula (VI) is preferably conducted in a solvent such as acetonitrile or a protic solvent (e.g., methanol, ethanol, propanol or isopropanol). While these solvents are preferred, other solvents which are inert with respect to the reactants and products and satisfactorily dissolve the subject materials can be employed. Examples of other suitable solvents are ether, tetrahydrofuran, dioxane, etc. Mild reaction temperatures, such as −5° C. to 45° C., are employed with ambient pressure and a reaction time of 0.5 to 8 hours.

The reaction of 5-aminopyrazole of formula (V) with imidate of formula (VI) yields a mixture of the pyrazole-imidate ester of formula (IIIA) and the pyrazole-imidine of formula (IIIB). The pyrazole-imidate of formula (IIIA) can be converted to the pyrazole-imidine of formula (IIIB) by treatment with ammonium chloride according to the following reaction scheme:

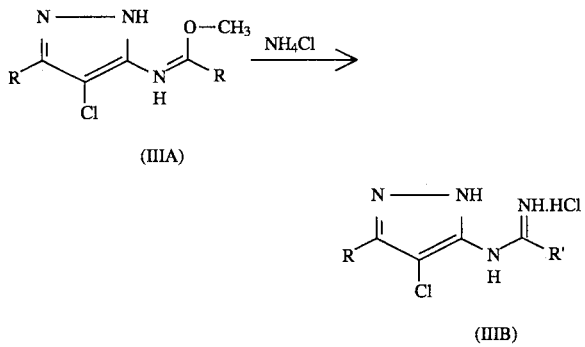

Thus, pure pyrazole-imidine of formula (IIIB) can be obtained from the reaction mixture by adding ammonium chloride to the mixture of (IIIA) an (IIIB). However, since the desired amidoxime of formula (II) can be prepared either from the imidate ester of formula (IIIA) or from the imidine of formula (IIIB), it is unnecessary to separate or isolate the crude mixture of (IIIA) and (IIIB). The crude mixture reacts directly with hydroxylamine to yield the desired amidoxime of formula (II).

A base is necessary for the step of formation of amidoxime of formula (II). Preferred bases are alkali metal salts of lower alcohols, such as sodium methoxide, lithium methoxide, sodium ethoxide, etc.

The pyrazolotriazole of formula (I) is obtained from the amidoxime of formula (II) by a cyclization reaction. In a preferred embodiment, this is achieved via an intermediate of structure (IV):

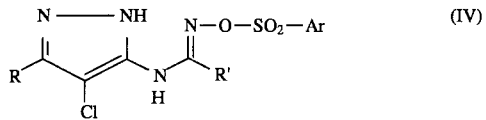

wherein Ar is a substituted aromatic ring. For example, the intermediate (IV) can be prepared by reacting the amidoxime of formula (II) with arylsulfonyl chloride in a suitable solvent, and this involves the activation of the oxime group towards the cyclization by attaching an efficient leaving group on the oxime functionality.

In this preferred embodiment, the preparation of the intermediate of formula (IV) is carried out in an aprotic solvent such as tetrahydrofuran, dioxane, ethyl acetate or methyl acetate, e.g. Other solvents which are inert with respect to the reactants and products can be employed. The reaction is conducted in the presence of a base. Preferred bases include aromatic amines such as substituted or unsubstituted pyridine and tertiary amines such as trialkylamines. The amount of the base may be 0.5 to 2 equivalent, and preferably, 1 equivalent. The preferred reaction temperature is −5° C. to 100° C., and the preferred reaction time is 1 to 10 hours.

The cyclization step from the intermediate of formula (IV) leading to the compound of formula (I) is preferably conducted in a protic solvent, such as the lower alcohols. Preferred alcohols include methanol, ethanol, propanol, isopropanol, etc. The cyclization is carried out in the presence of a base. The nature and the amount of the preferred bases are as previously defined for the preparation of the intermediate of formula (IV). The preferred reaction temperature is 40° C. to 100° C., and the preferred reaction time is 1 to 15 hours.

In the above formulae, R and R' independently represent hydrogen or a coupler substituent known in the art which typically promotes solubility, diffusion resistance or dye hue or dye stability of the dye formed upon reaction of the coupler with the oxidized color developing agent.

Examples of such substituent groups include: an alkyl group which may be straight or branched, and which may be substituted, such as methyl, ethyl, n-propyl, n-butyl, t-butyl, trifluoromethyl, tridecyl or 3-(2,4-di-t-amylphenoxy) propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenylthio or 2-butoxy-5-t-octylphenylthio; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substituted, such as N,N-dipropyl-sulfamoylamino or N-methyl-N-decylsulfamoylamino.

Additional examples of substituent groups include: a carbamoylamino group which may be substituted, such as N-butylcarbamoylamino or N,N-dimethyl-carbamoylamino; an alkoxycarbonylamino group which may be substituted, such as methoxycarbonylamino or tetradecyloxycarbonylamino; an aryloxycarbonylamino group which may be substituted, such as phenoxycaronylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy) acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycarbonyl; an alkenyl group carbon atoms which may be substituted; a carboxyl group which may be substituted; a sulfo group which may be substituted; hydroxyl; an amino group which may be substituted; or a carbonamido group which may be substituted.

Substituents for the above substituted R or R' groups include those that do not adversely affect the desired properties of the pyrazolotriazole coupler. Representative substituents for the substituted R or R' groups include: halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, an anilino group, a ureido group, an imido group, a sulfonylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group.

Generally, the above groups and substituents thereof which contain an alkyl group may include an alkyl group having 1 to 16 carbon atoms. The above groups and substituents thereof which contain an aryl group may include an aryl group having 6 to 8 carbon atoms, and the above groups and substituents which contain an alkenyl group may include an alkenyl group having 2 to 6 carbon atoms.

Preferably, R or R' represents hydrogen, an alkyl group, an aryl group, a carbonamido group, a sulfonamido group, a sulfone group, a thio group, a sulfoxide group, a ureido group or a multicyclic group.

Additionally, several of the above described R or R' groups constitute a ballast group, which is known in the photographic art as a radical of such size and configuration as to confer on the coupler molecule sufficient bulk to render the coupler substantially non-diffusible from the layer in which it is coated in a photographic element. Couplers of the invention may be attached to ballast groups, or to polymeric chains through one or more of the groups on the pyrazolotriazole nucleus. For example, one or more coupler moieties can be attached to the same ballast group. Representative ballast groups include substituted or unsubstituted alkyl, alkoxy, aryl or aryloxy groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido, and sulfamoyl substituents containing 1 to 30 carbon atoms and 6 to 30 carbon atoms, respectively, can be further substituted with such substituents.

Additionally, R or R' in formula (I) may constitute a reactive group which can be converted to a coupler substituent as defined above, thereby providing a dye-forming 1H-pyrazolo [1,5-b][1,2,4] triazole coupler. Thus, formula (I) includes compounds produced according to the method of the present invention which can then be further modified through the R or R' substituent to provide a desired dye-forming 1H-pyrazolo [1,5-b][1,2,4] triazole coupler by methods known in the art. For example, when R or R' is amino (—NH$_2$), the amine can be reacted with a group such as R"—CO—Cl, wherein R" is an alkyl, aryl, heterocyclic, alkoxy, aryloxy, alkylamino or arylamino group, to form a substituent of R"—CO—NH— on the pyrazolotriazole ring. An example of such a method is illustrated in U.S. Pat. No. 4,540,654, the disclosure of which is incorporated by reference.

Illustrative N-(4-chloropyrazolyl) amidoximes which can be produced according to the present invention are as follows. The representative compounds can be used to prepare corresponding 1H-pyrazolo [1,5-b][1,2,4] triazole compounds of formula (I). Each of the following compounds contain an R' group which is a ballast group in the corresponding coupler compound of formula (I).

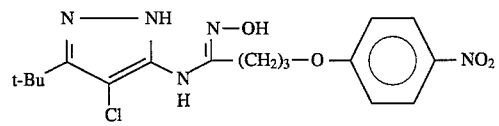

A-1

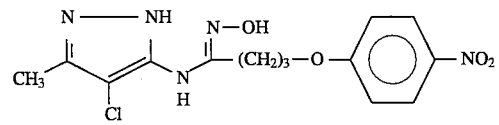

A-2

-continued
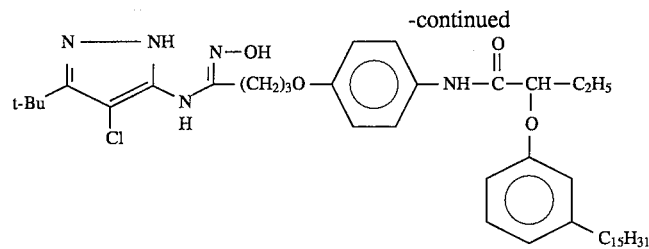 A-3
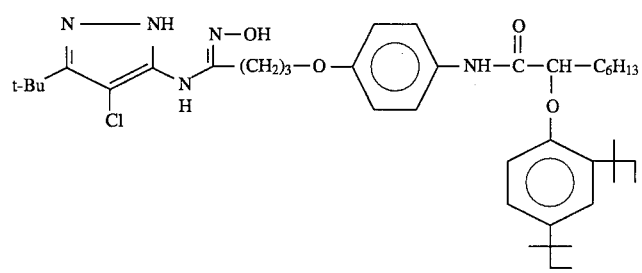 A-4
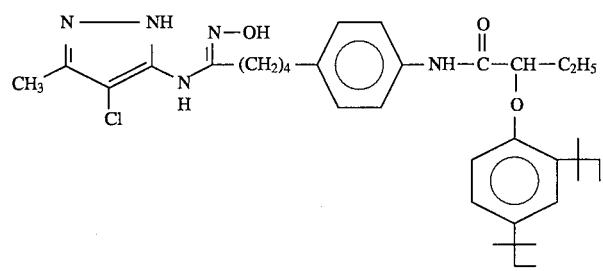 A-5
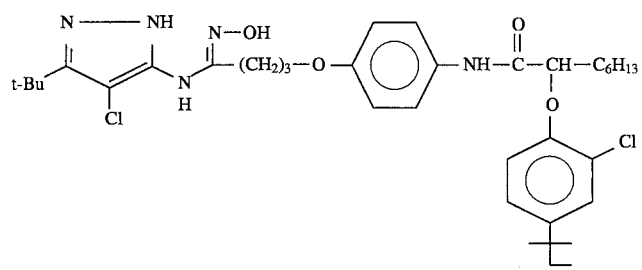 A-6
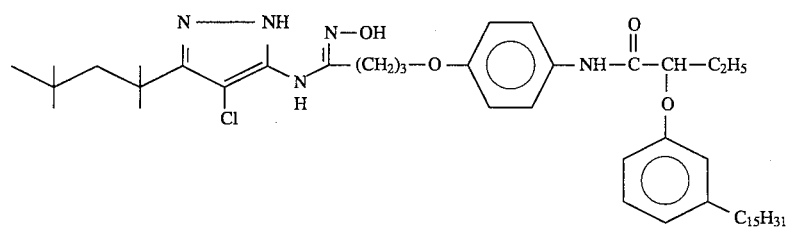 A-7
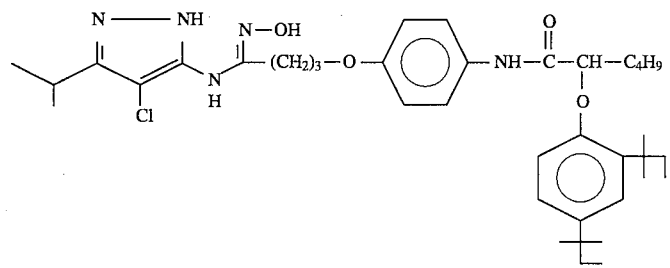 A-8

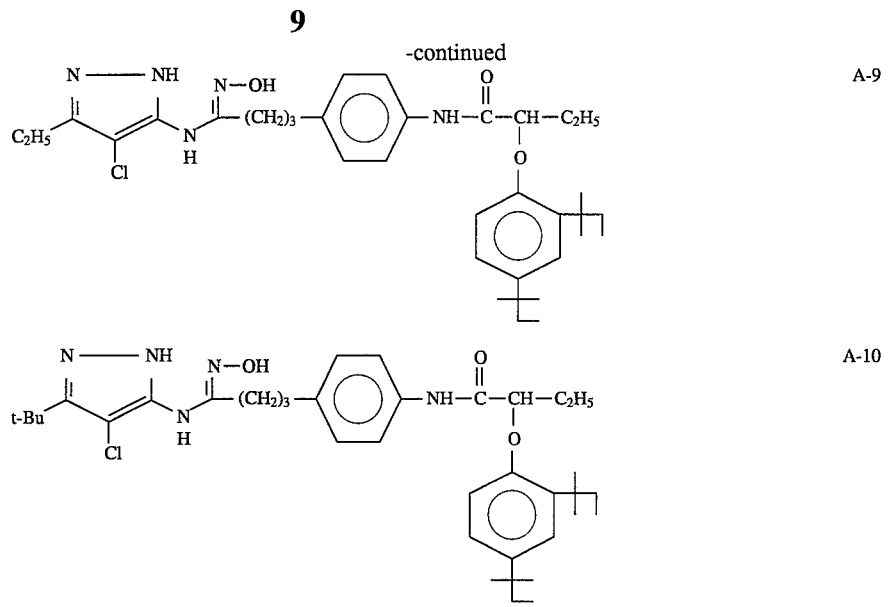
A-9
A-10
The following example further illustrates preferred embodiments of the present invention.
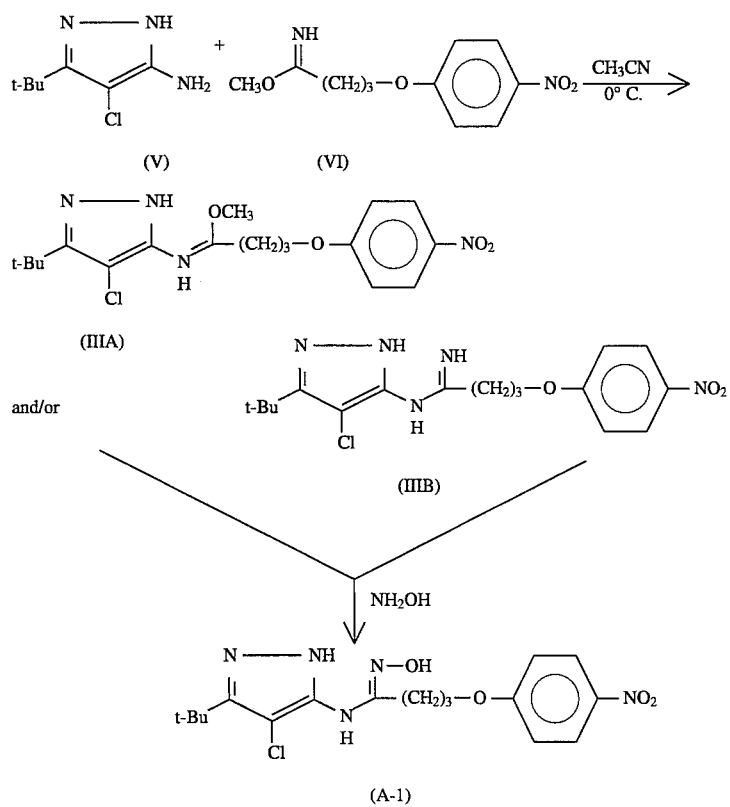

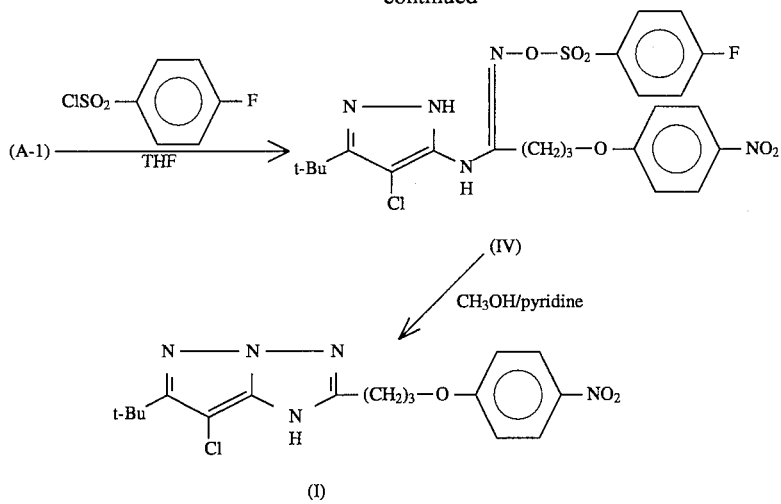

Preparation of Amidoxime (II)—Compound (A-1)

A suspension of 145 g (0.835 mol, 1.0 equiv) of 5-amino-3-tert-butyl-4-chloropyrazole (a compound of formula (V)) in 1000 ml of acetonitrile was cooled to 0° C., followed by the portionwise addition of 240.75 g (0.876 mol, 1.05 equiv) of the imidate (VI) disclosed above. The reaction mixture was stirred at 0° C. for 3 hours. The mixture was concentrated in vacuo to yield a solid. Two compounds identified as (IIIA) and (IIIB) as described above were present in the reaction mixture, as evidenced by thin layer chromatography analysis. In a separate experiment, the imidate of formula (IIIA) is converted to the imidine of formula (IIIB) by treatment with ammonium chloride.

To the solid, 1000 ml of methanol was added, followed by the addition of 63.79 g (0.918 mol, 1.10 equiv) of hydroxylamine hydrochloride. The stirred suspension was cooled to 0° C., followed by the portionwise addition of 198.4 g (0.918 mol, 1.10 equiv) of sodium methoxide (25% w/w in methanol). The reaction was allowed to warm to room temperature and stirred overnight. The mixture was poured into 6.5 liters of mixture of ice water. The mixture was stirred for 2 hours and the resulting solid was collected under suction, washed and dried in vacuo. The yield of the desired product (A-1) was 285.40 g (86%). All the analytical data were in agreement with the structure.

The following illustrates the cyclization of an amidoxime (II) to obtain a compound of formula (I).

Preparation of Coupler (I)

To a solution of 3.95 g (0.010 mol, 1 equiv) of the amidoxime (A-1) in 35 mol of dried tetrahydrofuran at ambient temperature was added 0.95 g (0.012 mol, 1.2 equiv) of pyridine, followed by the addition of 2.14 g (0.010 mol, 1 equiv) of para-fluorobenzene-sulfonylchloride.

The reaction mixture was stirred for 1 hour. At that time, no starting materials remained as evidenced by thin layer chromatograph (TLC) analysis of the reaction mixture. The solvent was removed in vacuo. To the residue was added 35 ml of methanol, followed by the addition of 0.94 g (0.012 mol, 1.2 equiv) of pyridine. The reaction mixture was heated at reflux for 2 hours. The cyclization was complete as observed by TLC. The reaction mixture was cooled to 20° C. and poured into a mixture of ice water. The solid was collected, washed and dried under suction. The crude product was purified by trituration in 45 ml of methanol to yield 2.88 g (78%) of the desired coupler of formula (I). All the analytical data were in agreement with the assigned structure.

The invention has been described in detail with particular reference to preferred embodiments thereof, but it will be understood that variations and modifications can be effected within the spirit and scope of the invention.

What is claimed is:

1. A process of preparing a 1H-pyrazolo[1,5-b][1,2,4] triazole compound of formula (I)

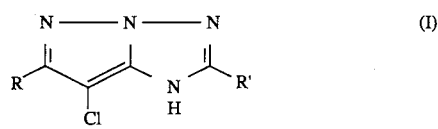

wherein R is selected from the group consisting of methyl, ethyl, n-propyl, n-butyl, and t-butyl and R' is

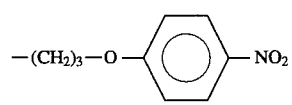

said process comprising reacting a compound of the formula (V)

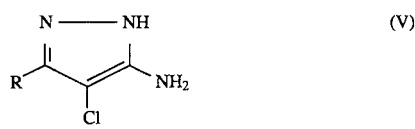

with a compound of the formula (VI)

to obtain compounds of formula (IIIA) and (IIIB)

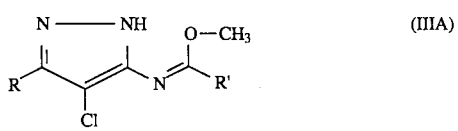

-continued

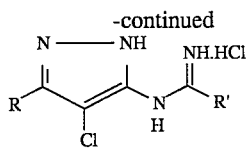 (IIIB)

converting, in the presence of a first base, the compounds of formula (IIIA) and (IIIB) to a compound of formula (II),

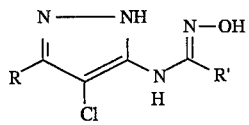 (II)

wherein R and R' are as previously defined, and reacting the compound of formula (II) with para-fluorobenzene-sulfonylchloride in the presence of a second base to obtain a compound of formula (IV)

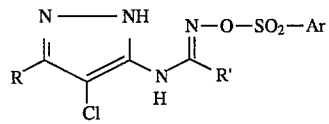 (IV)

and cyclizing the compound of formula (IV) in the presence of a third base to obtain the compound of formula (I).

2. The process of claim 1, wherein the first base is $NH_2OH$.

3. The process of claim 1, wherein the reaction of compounds (V) and (VI) is conducted in a solvent.

4. The process of claim 3, wherein the reaction of compounds (V) and (VI) is conducted at a temperature of −5° C. to 45° C.

* * * * *